US008858608B2

(12) United States Patent
Grewe et al.

(10) Patent No.: US 8,858,608 B2
(45) Date of Patent: Oct. 14, 2014

(54) LUBRICATION APPARATUS FOR A DELIVERY AND DEPLOYMENT DEVICE

(75) Inventors: David D. Grewe, West Lafayette, IN (US); James D. Purdy, Lafayette, IN (US); Kenneth Haselby, Battle Ground, IN (US); David Brocker, Carmel, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 1558 days.

(21) Appl. No.: 12/330,833

(22) Filed: Dec. 9, 2008

(65) Prior Publication Data

US 2009/0149938 A1    Jun. 11, 2009

Related U.S. Application Data

(60) Provisional application No. 61/012,550, filed on Dec. 10, 2007.

(51) Int. Cl.
*A61F 2/06* (2013.01)
*A61M 39/06* (2006.01)
*A61F 2/95* (2013.01)
*A61B 17/00* (2006.01)
*A61B 17/34* (2006.01)
*A61M 25/00* (2006.01)

(52) U.S. Cl.
CPC ......... *A61F 2/95* (2013.01); *A61B 2017/00292* (2013.01); *A61B 17/3498* (2013.01); *A61M 39/0606* (2013.01); *A61M 2039/068* (2013.01); *A61B 2017/00845* (2013.01); *A61M 2025/0062* (2013.01)

USPC .......................... 623/1.11; 606/194; 606/198

(58) Field of Classification Search
CPC ............ A61F 2/95; A61F 2/962; A61F 2/966
USPC .............. 623/1.11–1.12; 604/167.01–167.05, 604/265; 606/191, 198
See application file for complete search history.

(56) References Cited

U.S. PATENT DOCUMENTS

| 2,321,336 A | 6/1943 | Tondreau |
| 2,416,391 A | 2/1947 | Hixson |
| 2,844,351 A | 7/1958 | Smith |
| 3,185,179 A | 5/1965 | Harautuneian |
| 3,304,934 A | 2/1967 | Bautista |
| 3,329,390 A | 7/1967 | Hulsey |
| 3,599,637 A | 8/1971 | Schwartz |
| 4,000,739 A | 1/1977 | Stevens |
| 4,016,879 A | 4/1977 | Mellor |

(Continued)

FOREIGN PATENT DOCUMENTS

| EP | 0 344 907 A2 | 12/1989 |
| EP | 0 550 069 A1 | 7/1993 |

(Continued)

*Primary Examiner* — Katherine Dowe
*Assistant Examiner* — Michael Mendoza
(74) *Attorney, Agent, or Firm* — Brinks Gilson & Lione

(57) ABSTRACT

A delivery and deployment device comprises a sheath having a proximal end, a distal end, and a lumen disposed therebetween; a dilator having a distal end slidingly disposed within the sheath lumen; a valve assembly comprising a valve housing affixed to the sheath and a valve disposed within the housing between the sheath and the dilator; and a valve lubrication mechanism disposed between the valve and the dilator.

22 Claims, 10 Drawing Sheets

(56) References Cited

U.S. PATENT DOCUMENTS

| | | | |
|---|---|---|---|
| 4,063,555 A | 12/1977 | Ulinder | |
| 4,243,034 A | 1/1981 | Brandt | |
| 4,311,137 A | 1/1982 | Gerard | |
| 4,314,555 A | 2/1982 | Sagae | |
| 4,424,833 A | 1/1984 | Spector et al. | |
| 4,430,081 A | 2/1984 | Timmermans | |
| 4,540,411 A | 9/1985 | Bodicky | |
| 4,580,573 A | 4/1986 | Quinn | |
| 4,610,665 A | 9/1986 | Matsumoto et al. | |
| 4,610,674 A | 9/1986 | Suzuki et al. | |
| 4,626,245 A | 12/1986 | Weinstein | |
| 4,629,450 A | 12/1986 | Suzuki et al. | |
| 4,798,594 A | 1/1989 | Hillstead | |
| 4,895,565 A | 1/1990 | Hillstead | |
| 4,929,235 A | 5/1990 | Merry et al. | |
| 4,932,633 A | 6/1990 | Johnson et al. | |
| 4,978,341 A | 12/1990 | Niederhauser | |
| 5,000,745 A | 3/1991 | Guest et al. | |
| 5,006,113 A | 4/1991 | Fischer | |
| 5,009,391 A | 4/1991 | Steigerwald | |
| 5,053,013 A | 10/1991 | Ensminger et al. | |
| 5,066,285 A | 11/1991 | Hillstead | |
| 5,098,393 A | 3/1992 | Amplatz et al. | |
| 5,102,395 A | 4/1992 | Cheer et al. | |
| 5,125,903 A | 6/1992 | McLaughlin et al. | |
| 5,154,701 A | 10/1992 | Cheer et al. | |
| 5,158,553 A | 10/1992 | Berry et al. | |
| 5,167,637 A | 12/1992 | Okada et al. | |
| 5,176,652 A | 1/1993 | Littrell | |
| 5,211,370 A | 5/1993 | Powers | |
| 5,222,970 A * | 6/1993 | Reeves | 606/195 |
| 5,242,413 A | 9/1993 | Heiliger | |
| 5,256,150 A | 10/1993 | Quiachon et al. | |
| 5,267,966 A | 12/1993 | Paul | |
| 5,300,032 A | 4/1994 | Hibbs et al. | |
| 5,304,156 A | 4/1994 | Sylvanowicz et al. | |
| 5,350,363 A | 9/1994 | Goode et al. | |
| 5,350,364 A | 9/1994 | Stephens et al. | |
| 5,376,077 A | 12/1994 | Gomringer | |
| 5,395,349 A | 3/1995 | Quiachon et al. | |
| 5,395,352 A | 3/1995 | Penny | |
| 5,409,463 A | 4/1995 | Thomas et al. | |
| 5,484,418 A | 1/1996 | Quiachon et al. | |
| 5,538,505 A | 7/1996 | Weinstein et al. | |
| 5,613,956 A | 3/1997 | Patterson et al. | |
| 5,643,227 A | 7/1997 | Stevens | |
| 5,653,697 A | 8/1997 | Quiachon et al. | |
| 5,702,370 A | 12/1997 | Sylvanowicz et al. | |
| 5,779,681 A | 7/1998 | Bonn | |
| 5,895,376 A | 4/1999 | Schwartz et al. | |
| 5,935,122 A | 8/1999 | Fourkas et al. | |
| 6,042,588 A | 3/2000 | Munsinger et al. | |
| 6,054,421 A | 4/2000 | Lyons et al. | |
| 6,086,570 A | 7/2000 | Aboul-Hosn et al. | |
| 6,127,320 A | 10/2000 | Van Ooij et al. | |
| 6,179,863 B1 | 1/2001 | Kensey et al. | |
| 6,197,016 B1 | 3/2001 | Fourkas et al. | |
| 6,221,057 B1 | 4/2001 | Schwartz et al. | |
| 6,276,661 B1 | 8/2001 | Laird | |
| 6,379,372 B1 | 4/2002 | Dehdashtian et al. | |
| 6,416,499 B2 | 7/2002 | Paul, Jr. | |
| 6,562,049 B1 | 5/2003 | Norlander et al. | |
| 6,610,031 B1 | 8/2003 | Chin | |
| 6,652,480 B1 | 11/2003 | Imran et al. | |
| 6,663,599 B2 | 12/2003 | Osbourne et al. | |
| 6,740,101 B2 | 5/2004 | Houser et al. | |
| 6,966,896 B2 | 11/2005 | Kurth et al. | |
| 6,981,966 B2 | 1/2006 | Green et al. | |
| 7,172,580 B2 | 2/2007 | Hruska et al. | |
| 7,182,771 B1 | 2/2007 | Houser et al. | |
| 7,226,433 B2 | 6/2007 | Bonnette et al. | |
| 7,241,276 B2 | 7/2007 | Argentine et al. | |
| 7,241,308 B2 | 7/2007 | Andreas et al. | |
| 7,351,247 B2 | 4/2008 | Kupiecki et al. | |
| 2003/0018306 A1 * | 1/2003 | Bucay-Couto et al. | 604/265 |
| 2003/0144670 A1 | 7/2003 | Pavcnik et al. | |
| 2003/0216771 A1 | 11/2003 | Osypka et al. | |
| 2004/0176781 A1 | 9/2004 | Lindstrom et al. | |
| 2005/0060018 A1 | 3/2005 | Dittman | |
| 2005/0085890 A1 | 4/2005 | Rasmussen et al. | |
| 2005/0096605 A1 | 5/2005 | Green et al. | |
| 2005/0171470 A1 * | 8/2005 | Kucklick et al. | 604/96.01 |
| 2005/0171479 A1 | 8/2005 | Hruska et al. | |
| 2006/0052750 A1 | 3/2006 | Lenker et al. | |
| 2006/0282155 A1 * | 12/2006 | Fearn et al. | 623/1.12 |
| 2007/0026038 A1 | 2/2007 | Bayer et al. | |
| 2007/0088420 A1 | 4/2007 | Andreas et al. | |
| 2007/0106365 A1 | 5/2007 | Andreas et al. | |
| 2007/0185558 A1 * | 8/2007 | Hartley | 623/1.11 |
| 2007/0299518 A1 | 12/2007 | Ruane | |
| 2008/0294096 A1 | 11/2008 | Uber, III et al. | |
| 2009/0099636 A1 * | 4/2009 | Chanduszko et al. | 623/1.11 |

FOREIGN PATENT DOCUMENTS

| | | |
|---|---|---|
| EP | 0 755 694 A1 | 1/1997 |
| EP | 1 374 942 A1 | 1/2004 |
| WO | WO 98/53761 A1 | 12/1998 |
| WO | WO 99/26682 A1 | 6/1999 |

* cited by examiner

LUBRICATION APPARATUS FOR A DELIVERY AND DEPLOYMENT DEVICE

RELATED APPLICATIONS

This patent document claims the benefit of the filing date under 35 U.S.C. §119(e) of U.S. Provisional Patent Application Ser. No. 61/012,550, filed Dec. 10, 2007 which is herein incorporated by reference in its entirety.

BACKGROUND OF THE INVENTION

1. Field of the Invention

This invention relates to medical devices and procedures. In particular, this invention relates to devices and methods for reducing the forces encountered during delivery and deployment of medical devices, to alleviate or reduce physician fatigue.

2. Description of Related Art

Endoluminal prostheses, such as stents and stent grafts, are used for treating damaged or diseased body lumens such as the esophagus, bile duct, and blood vessels. For example, endoluminal prostheses may be used for repairing the diseased aorta including abdominal aortic aneurysms, thoracic aortic aneurysms, and other such aneurysms. The prosthesis is placed inside the body lumen and provides some or all of the functionality of the original, healthy vessel.

The deployment of endoluminal prostheses into the lumen of a patient from a remote location by the use of a catheter delivery and deployment device is well known in the art. For example, PCT Publication No. WO 98/53761 entitled "A Prosthesis and a Method and Means of Deploying a Prosthesis," which is incorporated herein by reference, proposes a delivery and deployment system for an endoluminal prosthesis. The prosthesis is radially compressed onto a delivery catheter and is covered by an outer sheath. To deploy the system, the operator slides the outer sheath over the delivery catheter, thereby exposing the prosthesis. The prosthesis expands outwardly upon removal of the sheath. Such a delivery and deployment device has been referred to as a "push-pull" system because as the operator pulls the sheath proximally in relation to the delivery catheter, the delivery catheter pushes the prosthesis out of the sheath.

Devices, such as the ones described in WO 98/53761 have several advantages. To deploy the prosthesis, the operator can directly manipulate the sheath and the delivery catheter. This provides the operator with a relatively high degree of control during the procedure. Further, such devices may be compact and may have a relatively uniform, low-diameter radial profile, allowing for atraumatic access and delivery.

With some catheter delivery and deployment devices, the force required to withdraw the sheath may be relatively high. The withdrawal force is a function of various factors including, for example, frictional resistance caused by the sliding engagement between components of the system such as the sheath, the delivery catheter, the prosthesis, and the hemostatic valve assembly. A delivery and deployment device may require as much as 100 Newtons or approximately 22.5 pounds of force to deploy. This force is transferred to the physician performing the procedure. Such force can easily tire an operator and, accordingly, is highly undesirable.

Motors, springs, gears, and other such devices, have been proposed to reduce the force required to withdraw the sheath over the delivery catheter. Examples of such devices are described in U.S. application Ser. No. 11/764,969, entitled "Prosthesis Delivery and Deployment Device," and U.S. App. Ser. No. 60/950,001, entitled "Prosthesis Delivery and Deployment Device," each of which are herein incorporated by reference. Additionally, various lubricants and lubrication methods have been proposed to reduce the force required to insert a catheter into a sheath. For example, in some methods a lubricant, such as a medical-grade silicone, is applied to the catheter before the catheter is inserted into the sheath. The lubricated catheter is then inserted into the sheath through a hemostatic valve. The force required to place the catheter is reduced by virtue of the presence of the lubricant on the catheter.

Once the delivery catheter is placed within the sheath lumen, the delivery and deployment device may be stored for days, weeks, or even months, before the device is used. During this time, the valve presses against the delivery catheter and forms a static bond. The force required to overcome this static bond often constitutes a significant portion of the entire sheath withdrawal force. The lubrication methods described above rely on the sliding interaction between the catheter and the valve and, therefore, are advantageous for reducing dynamic or sliding friction. However, these methods are generally ineffective for reducing static friction. Thus, there is a need for alternative devices and methods for decreasing the sheath withdrawal resistance of a delivery and deployment device, resulting from both dynamic and static friction.

SUMMARY

Various delivery and deployment devices and methods are described that alleviate sheath withdrawal resistance resulting from both dynamic and static friction. In one example, a delivery and deployment device is provided and includes a sheath having a sheath lumen, a dilator slidingly disposed within the sheath lumen, a valve assembly having a valve housing affixed to the sheath and a valve disposed within the housing between the sheath and the dilator, and a novel valve lubrication mechanism. The valve lubrication mechanism may be disposed between the valve and the dilator and have an inner surface in sliding contact with the outer surface of the dilator and an outer surface in sliding contact with the valve.

The valve lubrication mechanism may include, for example, a sleeve having an inner surface in sliding contact with the outer surface of the dilator and an outer surface in sliding contact with the valve. In some examples, the outer surface of the sleeve may include one or more grooves for receiving a lubricant. For example, the outer surface of the sleeve may include one or more circumferential grooves, such as helical grooves or annular grooves. Alternatively, or additionally, the outer surface of the sleeve may include one or more longitudinal grooves. In some examples, the dilator may also include one or more grooves for receiving a lubricant. Like the sleeve, the dilator may comprise longitudinal and/or circumferential grooves.

In addition to one or more of the features described above, a delivery and deployment device may further include a lubricant, which may be coated on the outer surface of the dilator. Any suitable biocompatible lubricant may be used. In some examples, the lubricant may be selected from the group consisting of hyaluronic acid, polyvinylpyrolidone, and polyacrylamide. The lubricant may be water-soluble.

In another example, a delivery and deployment device may be provided and include a sheath, a dilator, and a valve assembly, as described above. The device may further include a novel means for lubricating the contact surface between the valve and the dilator. Various lubricating means are described and depicted throughout the specification and in the figures. For example, the lubricating means may include a sleeve having an inner surface in sliding contact with the outer surface of the dilator and an outer surface in sliding contact with the valve. The outer surface of the sleeve may have one or more grooves for receiving a lubricant.

In another example, a method of reducing the deployment force of a prosthesis delivery and deployment system is described. The method may be used, for example, to reduce the deployment force of a delivery and deployment system comprising an elongate sheath, a dilator slidingly disposed within a lumen of the sheath, and a valve assembly comprising a valve for forming a hemostatic seal between the sheath and the dilator. The method includes the steps of providing a novel valve lubrication mechanism and sliding the valve lubrication mechanism between the dilator and the valve to lubricate the contact surface between the dilator and the valve.

Other methods may further comprise one or more of the steps of applying a lubricant to the valve lubrication mechanism, applying a lubricant to the dilator, evaporating a solvent from the lubricant to form a coating, and re-solubilizing the coating.

DETAILED DESCRIPTION OF PREFERRED EMBODIMENTS

Throughout the specification, the terms "distal" and "distally" shall denote a position, direction, or orientation that is generally toward the patient. Accordingly, the terms "proximal" and "proximally" shall denote a position, direction, or orientation that is generally away from the patient.

Figure 1:
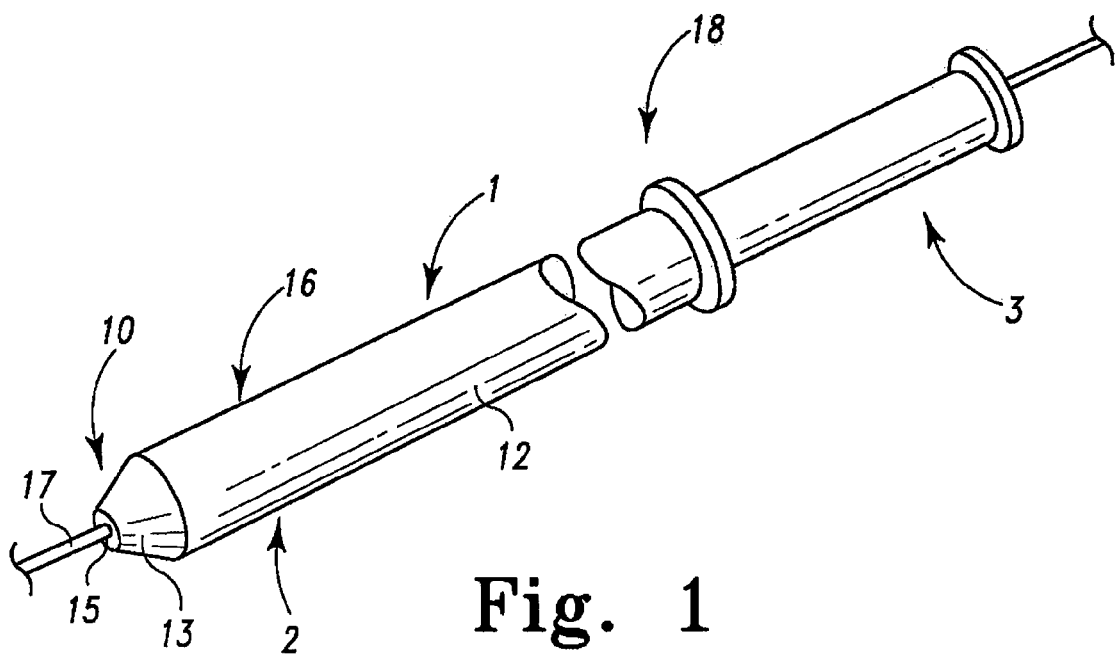
FIG. 1 is a perspective view of a delivery and deployment device.
Figure 2:
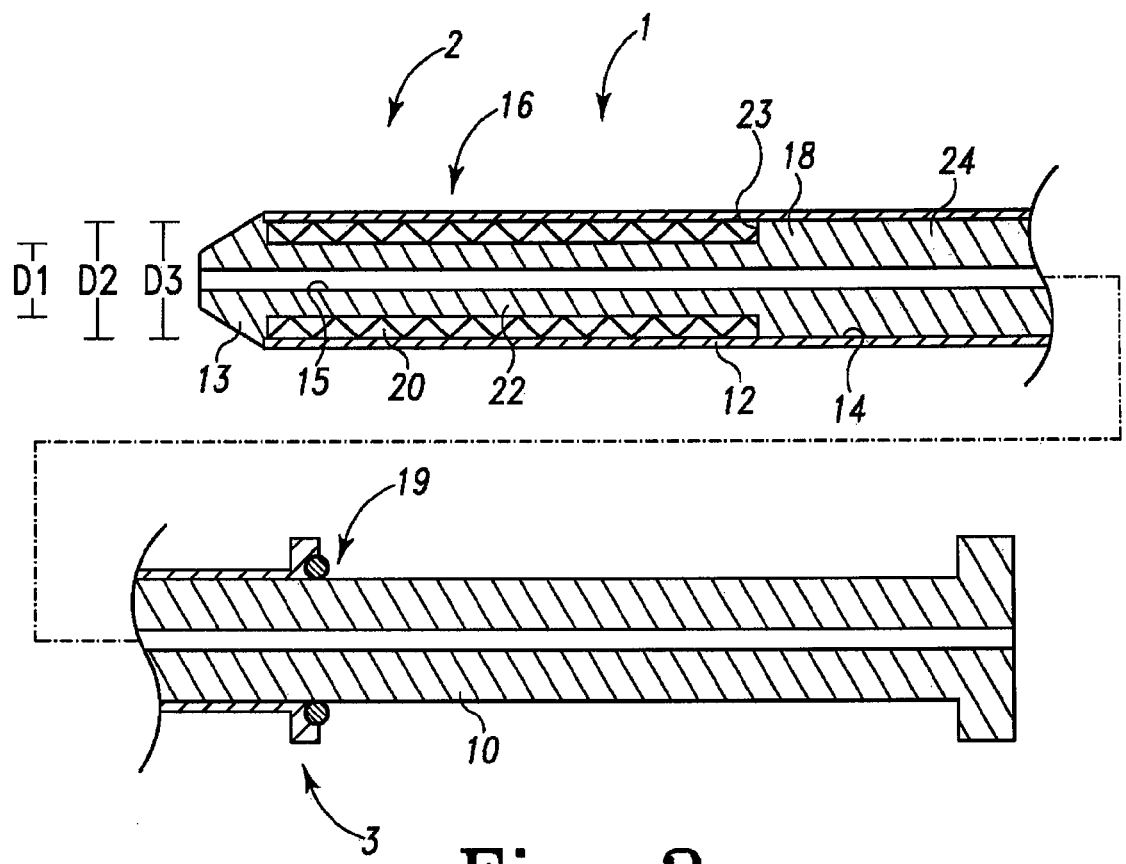
FIG. 2 is a cross-sectional view of the device of FIG. 1.
Figure 3:
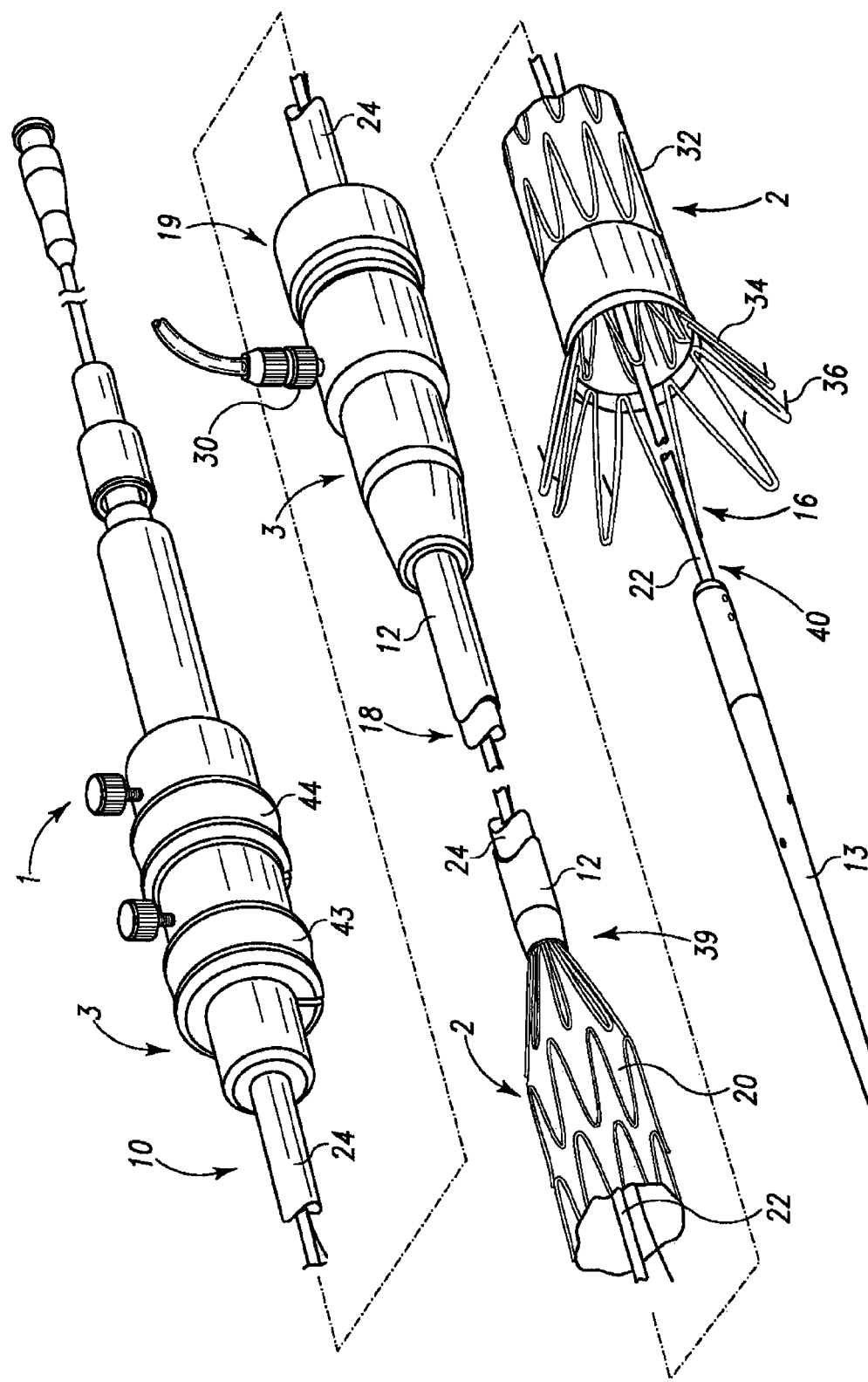
FIG. 3 is a perspective view of selected segments of another delivery and deployment device including a partially-deployed prosthesis.

FIGS. 1-3 show various exemplary devices 1 for delivering and deploying an expandable endoluminal prosthesis 20 in a body lumen. The device 1 includes a prosthesis delivery section 2 and an external manipulation section 3. The delivery section 2 travels through the body lumen during the procedure and delivers the prosthesis to a desired deployment site. The external manipulation section 3 stays outside of the body during the procedure. The external manipulation section 3 can be manipulated by the operator to position and release or deploy the prosthesis 20 into the body lumen.

The delivery and deployment device 1 includes a delivery catheter 10 and a sheath 12. The delivery catheter 10 and the sheath 12 are configured to selectively retain and release an expandable prosthesis 20. The delivery catheter 10 has a proximal end and a distal end. The distal end of the delivery catheter comprises a dilator head 13. The dilator head 13 is distally tapered to provide for atraumatic insertion into the body lumen (not shown). A guidewire lumen 15 extends longitudinally through the delivery catheter 10 between the proximal and distal ends. The delivery catheter 10 is configured to receive a guidewire 17 via the guidewire lumen 15 as shown in FIG. 1.

The delivery catheter 10 includes a prosthesis receiving portion 16 and a prosthesis release portion 18, as shown in FIG. 2. The receiving portion 16 is disposed on a distal portion of the delivery catheter 10 and is configured to receive the prosthesis 20 in a radially compressed configuration. As shown in FIGS. 2 and 3, the receiving portion 16 may include a catheter 22 having a longitudinally uniform external diameter D1.

The release portion 18 of the delivery catheter 10 is disposed generally proximally of the prosthesis 20. The release portion 18 can be manipulated, along with the sheath 12, to selectively deliver and deploy the prosthesis 20 in the body lumen. As shown in FIGS. 2 and 3, the release portion 18 may include a dilator catheter 24 having a longitudinally uniform external diameter D2. Dilator 24 may have a diameter D2 that is greater than diameter D1. As shown in FIGS. 2 and 3, the release portion 18 includes a distal-facing annular abutment surface 23 at the transition between catheters 22 and 24. The annular abutment surface 23 faces the proximal end of the prosthesis 20 and is configured to contact the proximal end of the prosthesis 20 during deployment, allowing the delivery catheter 10 to push the prosthesis 20 distally as the sheath 12 is pulled proximally in relation thereto. The delivery catheter 10 may comprise a single unitary structure as shown in FIG. 2. Alternatively, the delivery catheter 10 may comprise a plurality of slideably interconnected catheters 22, 24 as shown in FIG. 3.

The sheath 12 includes an elongate tubular body having a proximal and distal end and a sheath lumen 14. The sheath lumen 14 has a generally constant diameter between the proximal and distal ends. The sheath 12 extends proximally from the delivery section 2 to the user manipulation section 3. The delivery catheter 10 is slideably disposed within lumen 14. The sheath 12 releasably covers and retains the prosthesis 20 in a radially reduced configuration. The dilator head 13 and the sheath 20 preferably form a generally smooth transition so as to prevent trauma to the body lumen during delivery and deployment. The distal end of the sheath 12 travels within the body lumen during a procedure. The proximal end of the sheath 12 is configured to remain outside of the body during the procedure and can be directly manipulated by the operator to deploy the prosthesis 20.

The sheath 12 may have a length, as shown in FIG. 3, that is significantly greater than the length of the prosthesis 20. For example, the sheath 12 may have a length that is two or more times greater than the length of the prosthesis 20. Alternatively, the sheath 12 may have a length that is generally equal to or only somewhat greater than the length of the prosthesis. The sheath 12 may have a uniform internal diameter D3. The internal diameter D3 is generally equal to the external diameter D2 of dilator 24 so that the inner surface of the sheath 12 slidingly engages the delivery catheter 10.

The sheath may be made of any suitable biocompatible material, for example PTFE, nylon, or polyethylene. The sheath may optionally include a flat wire coil (not shown) to provide the sheath with additional flexibility and kink-resistance. U.S. Pat. No. 5,380,304 and U.S. Published Patent Application No. 2001/0034514 A1, incorporated herein by reference, propose various reinforced sheaths and methods of making the same that may be used in the present invention.

As shown in FIG. 3, the prosthesis 20 may include a stent graft having a plurality of self-expanding stents 32. The stents 32 cause the prosthesis 20 to expand during its release from the device 1. The stents 32 may cover and/or may be at least partially covered by a graft material. The prosthesis 20 also may include an anchor, such as an exposed stent 34, for anchoring the prosthesis 20 in the body lumen. As shown in FIG. 3, the stent 34 may be a self-expanding zigzag stent and may comprise barbs 36, or other anchoring mechanisms, that extend from the stent. When the anchor 34 is released, the barbs 36, or other anchoring mechanisms, engage the surrounding lumen.

Various graft materials and configurations may be used in the present invention. Suitable graft configurations include, but are not limited to films, coatings, sheets of biocompatible fabrics, non-woven materials and porous materials. Examples of suitable graft materials include polyesters, such as poly(ethylene terephthalate), polylactide, polyglycolide and copolymers thereof; fluorinated polymers, such as polytetrafluoroethylene (PTFE), expanded PTFE and poly(vinylidene fluoride); polysiloxanes, including polydimethyl siloxane; and polyurethanes, including polyetherurethanes, polyurethane ureas, polyetherurethane ureas, polyurethanes containing carbonate linkages and polyurethanes containing siloxane segments.

Stents may be self-expanding or balloon-expandable. A balloon-expandable stent or stent portion may be combined with a self-expanding stent or stent portion. Self-expanding stents can be made of stainless steel, materials with elastic memory properties, such as NITINOL, or any other suitable material. A suitable self-expanding stent includes Z-STENTS®, which are available from Cook Incorporated, Bloomington, Ind., USA. Balloon-expandable stents may be made of various materials including, but not limited to, stainless steel (typically 316LSS, CoCr, Etc.).

The prosthesis 20 is retained in a radially reduced configuration between the delivery catheter 10 and the sheath 12. The sheath 12 is slideably disposed over the prosthesis 20 and the delivery catheter 10 in a proximal and a distal direction. The sheath 12 may be slid proximally with respect to the delivery catheter 10 and the prosthesis 20 to expose the prosthesis. To deploy the prosthesis 20, the operator slides the sheath 12 proximally while applying distal pressure to the delivery catheter 10 via dilator 24. Dilator 24 pushes the prosthesis 20 distally via the annular abutment surface 23 while the sheath 12 slides proximally in relation thereto. As the sheath 12 slides proximally, dilator 24 pushes the prosthesis 20 distally from the receiving portion 16 and into the body lumen.

The delivery and deployment device 1 may optionally include deployment control mechanisms 39, 40 as shown in FIG. 3. Proximal control mechanism 39 releasably retains the proximal end of the prosthesis 20 and distal control mechanism 40 releasably retains the distal end of the prosthesis 20. Proximal control mechanism 39 may include at least one trigger wire 41 (not shown) that releasably couples the proximal end of the prosthesis 20 to the delivery catheter 10. Likewise, the distal control mechanism 40 may include at least one trigger wire 42 (not shown) that releasably couples the distal end of the prosthesis 20 to the delivery catheter 10. The trigger wires 41, 42 extend proximally to the external manipulation section 3 where they are coupled to trigger release devices 43, 44. Trigger release devices 43, 44 are configured to selectively decouple the proximal and distal ends of the prosthesis from the delivery catheter 10, respectively. Various prosthesis retention devices, configurations, and methods of use are disclosed in PCT Publication No. WO 98/53761, previously incorporated by reference.

Figure 4:
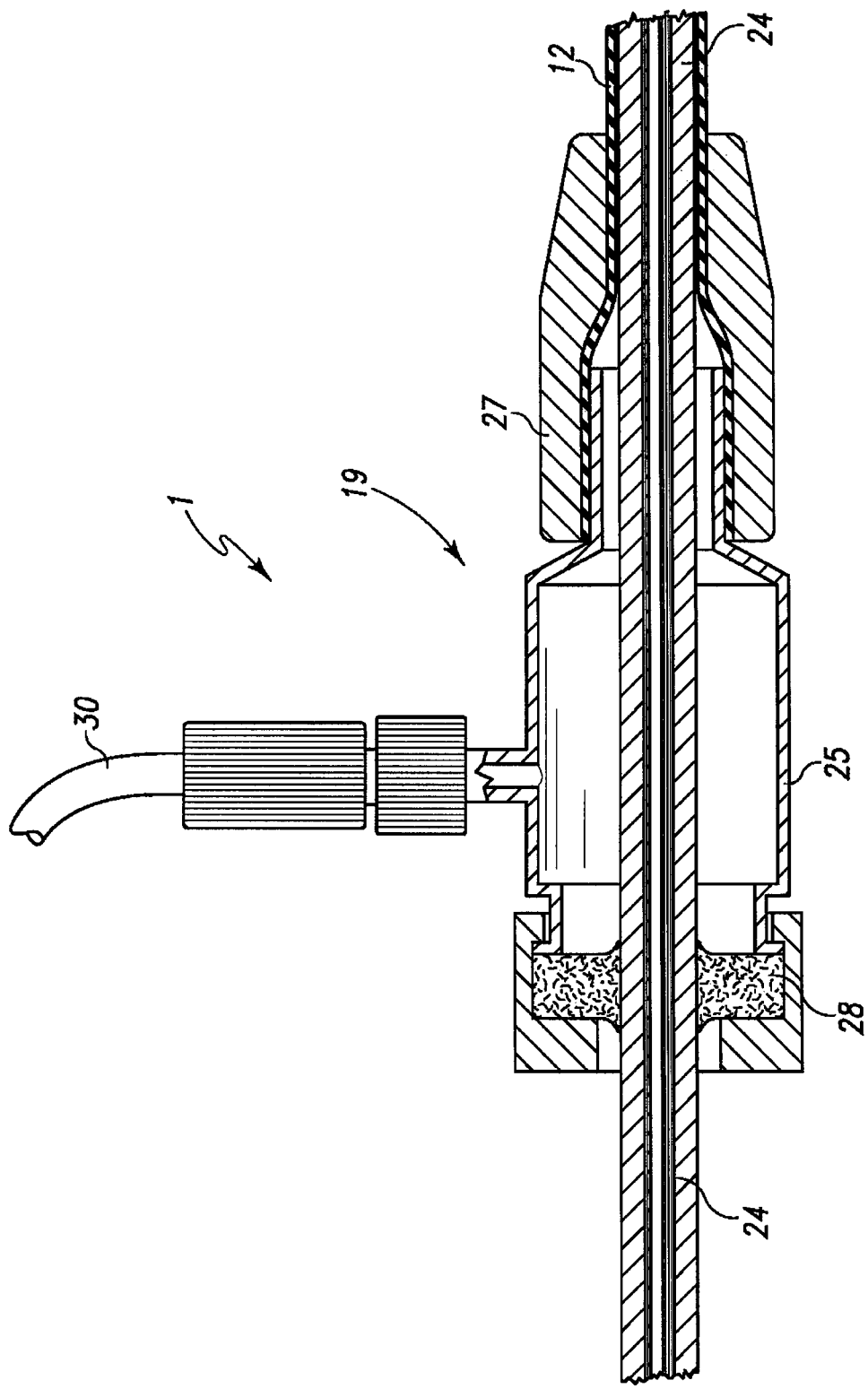
FIG. 4 is a cross-sectional view of the device of FIG. 3 around the hemostatic valve assembly.

The delivery and deployment device 1 may further include a valve assembly 19, as shown in FIGS. 3 and 4. As shown in these figures, the assembly may include a housing 25 and a clamping collar 27 that attaches the housing 25 to the sheath 12. A valve 28 is disposed within the housing 25 between the sheath 12 and the dilator 24. The valve 28 is fixedly connected to the housing 25 and is slideably disposed with respect to the dilator 24. During a procedure, the valve 28 sealingly engages the dilator 24 to control blood loss between the delivery catheter 10 and the sheath 12. The hemostatic sealing device 19 may also include a side tube 30 that facilitates the introduction of medical reagents between the delivery catheter 10 and the sheath 12.

The valve may include, for example, one or more check valves and/or one or more "iris"-type valves. Suitable check valves include CHECK-FLO® valves. Suitable valve assemblies include the CAPTOR® Hemostatic Valve. Each are available from Cook Incorporated, Bloomington, Ind., USA. Other suitable valves and valve assemblies are described in the patent literature, for example, in U.S. Pat. No. 4,430,081, entitled "Hemostasis Sheath," U.S. Pat. No. 5,006,113, entitled "Hemostasis Cannula," U.S. Pat. No. 5,267,966, entitled "Hemostasis Cannula and Method of Making a Valve for Same," U.S. Pat. No. 6,416,499, entitled "Medical Fluid Flow Control Valve," U.S. Pat. No. 6,663,599, entitled "Hemostasis Cannula," and U.S. Pat. No. 7,172,580, entitled "Hemostatic Valve Assembly." Each of the foregoing patents is herein incorporated by reference.

A primary function of the valve assembly 19 is controlling and limiting blood loss during a procedure. Accordingly, the valve 28 preferably forms a tight sealing engagement with the dilator 24. A tight seal may be provided, for example, by maximizing the area of surface contact between the valve 28 and the dilator 24 and by maximizing the pressure asserted by the valve against the dilator. In general, as the quality of the seal improves, the friction between the sheath 12 and the delivery catheter 10 may increase, thereby increasing the force required to slide the valve assembly 19, and therefore the sheath 12, over the delivery catheter 10. This "valve" resistance may constitute a significant component of the sheath withdrawal force.

A number of experiments were conducted with the goal of reducing this "valve" resistance, while maintaining optimal valve performance and avoiding problems associated with back-bleeding or blood loss. For example, in some experiments, a lubricant was applied to the dilator within the valve housing. In other experiments, a lubricant was applied to the dilator, outside of the housing, to lubricate the region that would be traversed by the valve during sheath withdrawal.

Figure 5:
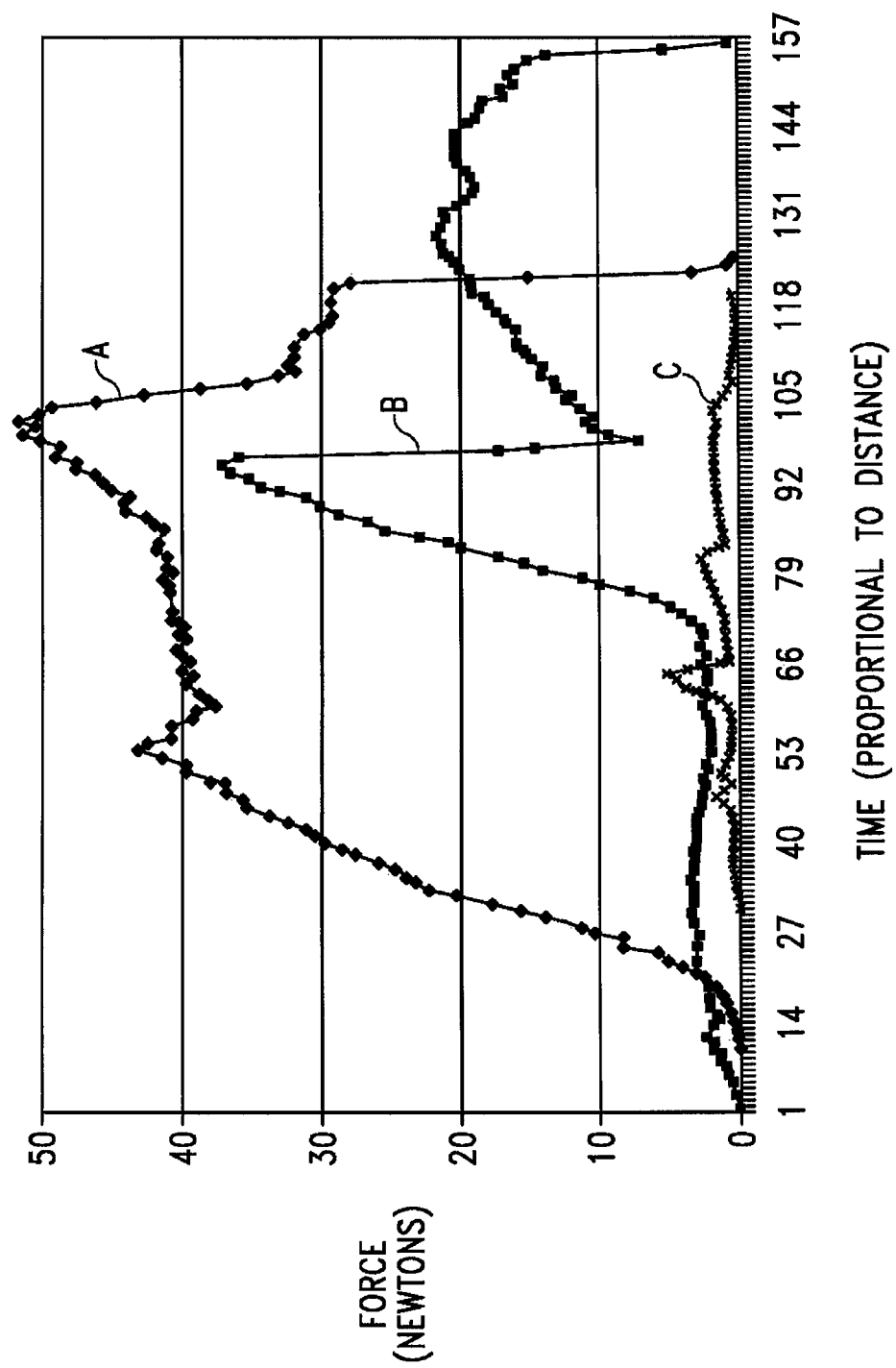
FIG. 5 is a graph depicting the withdrawal force of various delivery and deployment devices.

FIG. 5 shows a graph of the sheath withdrawal force as a function of time (which is proportional to sheath withdrawal distance). Curve A depicts the results of an experiment where the housing of the device was irrigated with a saline solution. In this experiment, the peak withdrawal force was greater than 50 Newtons. Curve B depicts the result of another experiment where the valve and dilator were irrigated with a saline solution, outside of the valve housing, to lubricate the region that would be traversed by the valve. In this experiment, the peak withdrawal force was less than 40 Newtons. Other lubricants were tested, including hyaluronic acid, polyvinylpyrolidone, Liposyn® III, and olive oil.

The results of these experiments indicated that it was possible to reduce at least some of the "valve" resistance by applying a lubricant to the dilator. Although there were measurable benefits of the methods employed during these experiments, there were also various challenges. For example, in some experiments, there was a high initial resistance, presumably due to static friction between the valve and the dilator. In other experiments, (e.g., the experiment depicted in curve B), the sheath withdrawal force was erratic and non-uniform, presumably due to inadequate lubricant application between the valve and the dilator. In addition, it was difficult to apply a lubricant to the dilator during sheath withdrawal and, in some cases, a second person was required to perform this step. Moreover, this approach was messy and, in some cases, the delivery catheter and valve housing became slippery and difficult to grasp. Thus, while these methods provided some alleviation of the force, there clearly remained a need for improved devices and methods for reducing both static and dynamic friction between the valve and the delivery catheter.

The inventors theorized that the static friction force could be substantially reduced by lubricating the contact surface between the valve and the dilator, immediately prior to withdrawing the sheath over the dilator. However, adequate lubrication of this contact surface was difficult due to the tight seal and static bond between the valve and dilator. Accordingly, the inventors developed novel valve lubrication mechanisms and methods for lubricating this contact surface.

For example, a lubrication mechanism may be provided that is slideably disposed between the valve and the dilator. In this example, the mechanism has an inner surface in sliding contact with the outer surface of the dilator and an outer surface in sliding contact with the valve. The lubrication mechanism is adapted to receive a lubricant. To lubricate the valve, the physician may slide the lubrication mechanism along the dilator, and through the valve, so that lubricant that is present on the lubrication mechanism may traverse and lubricate the valve and the dilator-valve contact surface. In some examples, described in further detail below, a solid lubricant, such as a dried or evaporated lubricant coating, may be provided on the dilator and a liquid lubricant, such as saline solution, may be applied via the lubrication mechanism, to wet and/or solubilize the coating. Various suitable lubricants may be used in connection with the inventive devices and methods disclosed herein and include, for example, saline solutions, hyaluronic acid, polyvinylpyrolidone, polyacrylamide, silicones, lipid emulsions such as Liposyn® (available from Abbott Laboratories) and Rotaglide™ (available from Boston Scientific), and the like.

Figure 6:
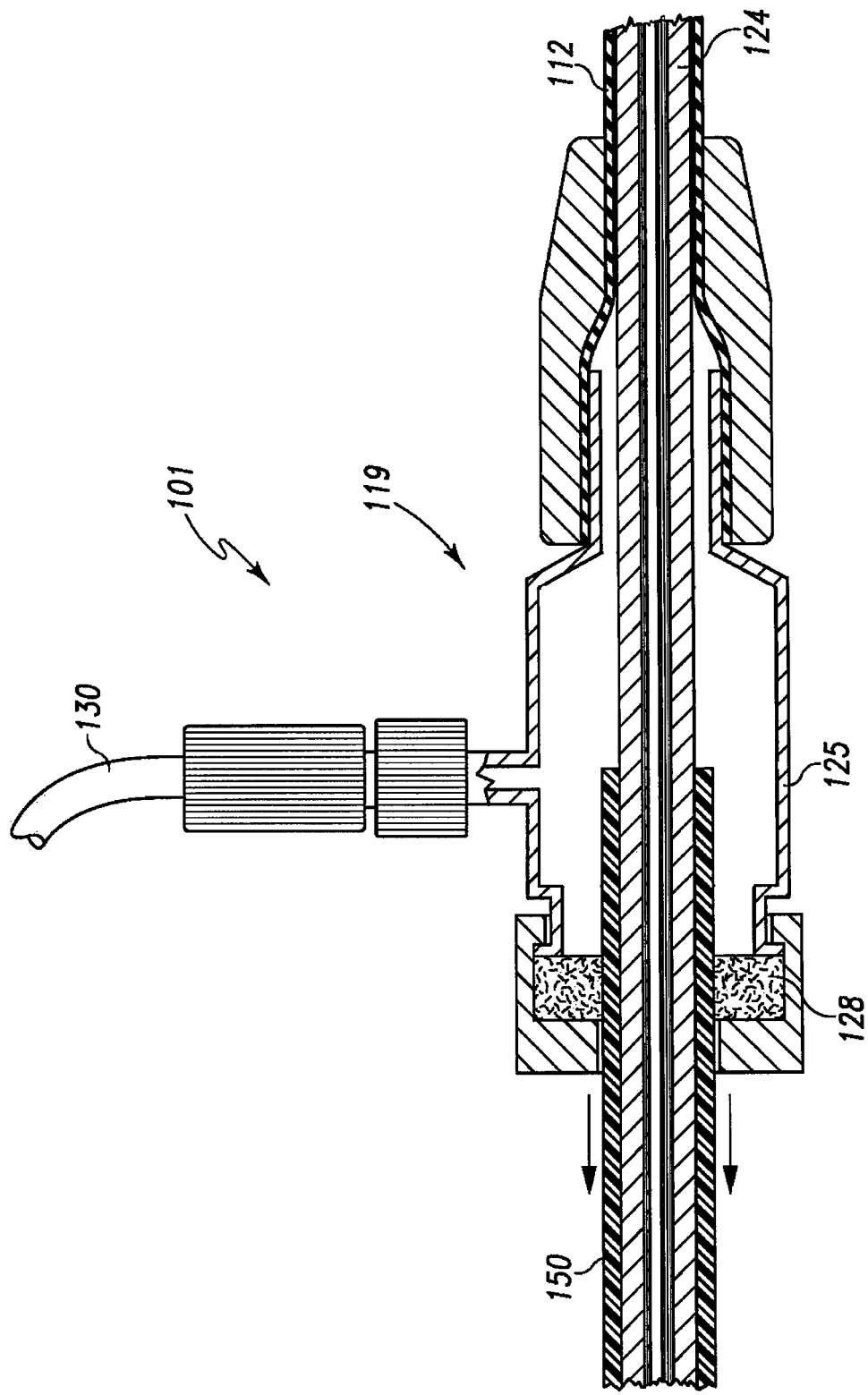
FIGS. 6-9 show various features that may be used separately, or in combination, to reduce the sheath withdrawal force of a delivery and deployment device.

FIG. 6 illustrates a delivery and deployment device 101 that is similar to the devices shown in FIGS. 1-4 and described above. The device comprises a sheath 112 and a dilator 124 slidingly disposed within a lumen of the sheath 112. A valve assembly 119 is attached to the sheath 112 and comprises a housing 125 and a valve 128 disposed within the housing 125 between the sheath 112 and the dilator 124. The device 101 further comprises a sleeve 150 that is slidingly disposed about the dilator 124. As shown in FIG. 6, the sleeve 150 may be positioned so that its outer surface is in sliding contact with the valve 128. In FIG. 6, the distal end of the sleeve 150 is disposed within the housing 125, distal to the valve 128, and the proximal end of the sleeve 150 is disposed outside of the housing 125, proximal to the valve 128. The sleeve preferably comprises a handle, or the like, to manipulate and slide the sleeve along the dilator and through the valve assembly.

In some examples, the sleeve 150 may comprise a peel-away sleeve such as the PEEL-AWAY® sheath, which is available from Cook Incorporated, Bloomington, Ind., USA. An example of a delivery and deployment device that utilizes a peel-away sleeve is the H&L-B ONE-SHOT™ Introduction System, which is also available from Cook Incorporated. Such a sleeve typically has a smooth and lubricious surface, for example, to allow the sleeve to slide easily between the dilator and valve and is provided, for example, to shield and protect the valve during loading of the dilator into the sheath. The sleeve is typically provided with the delivery and deployment device and is removed prior to use of the device.

Figure 7:
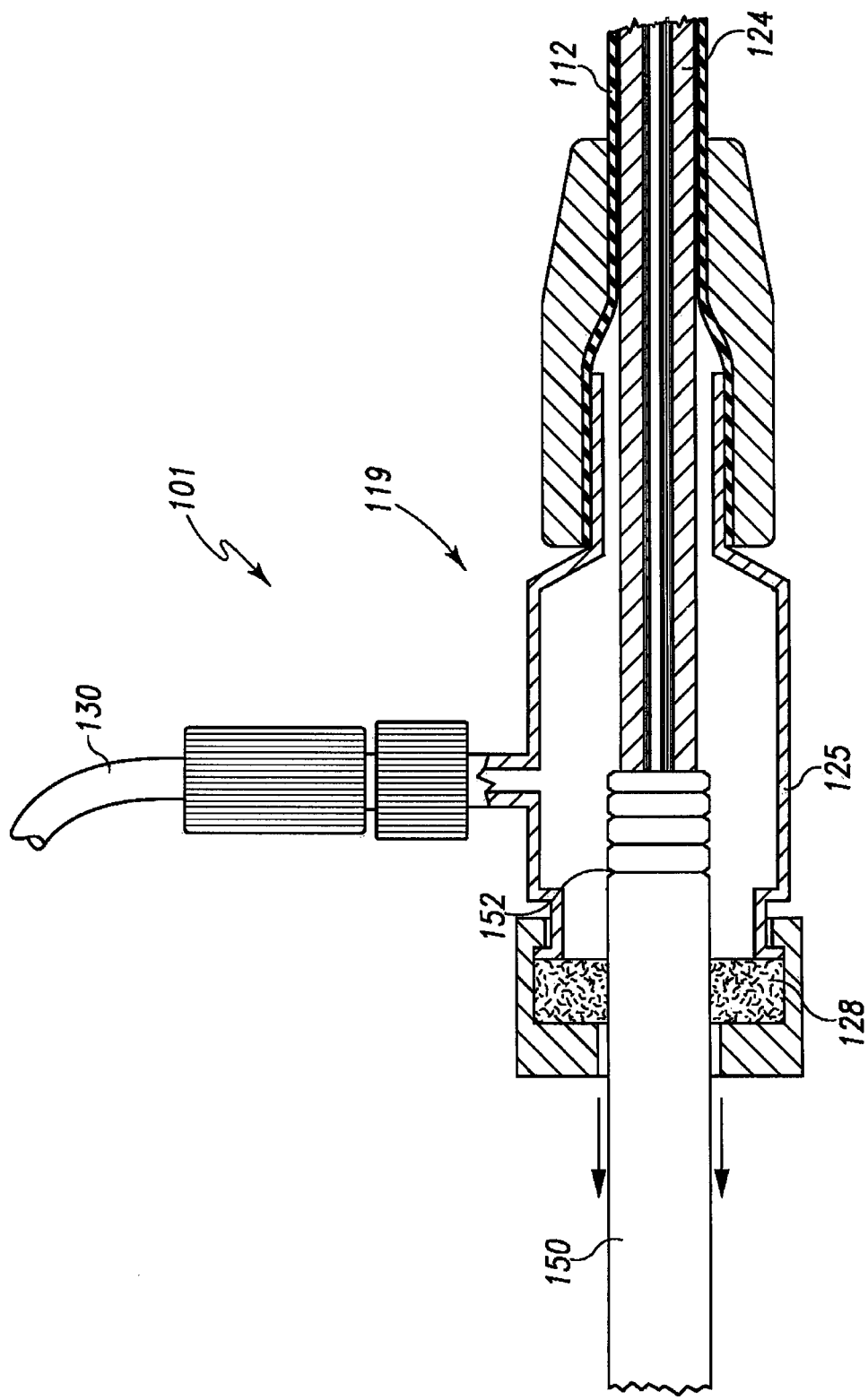
Figure 8:
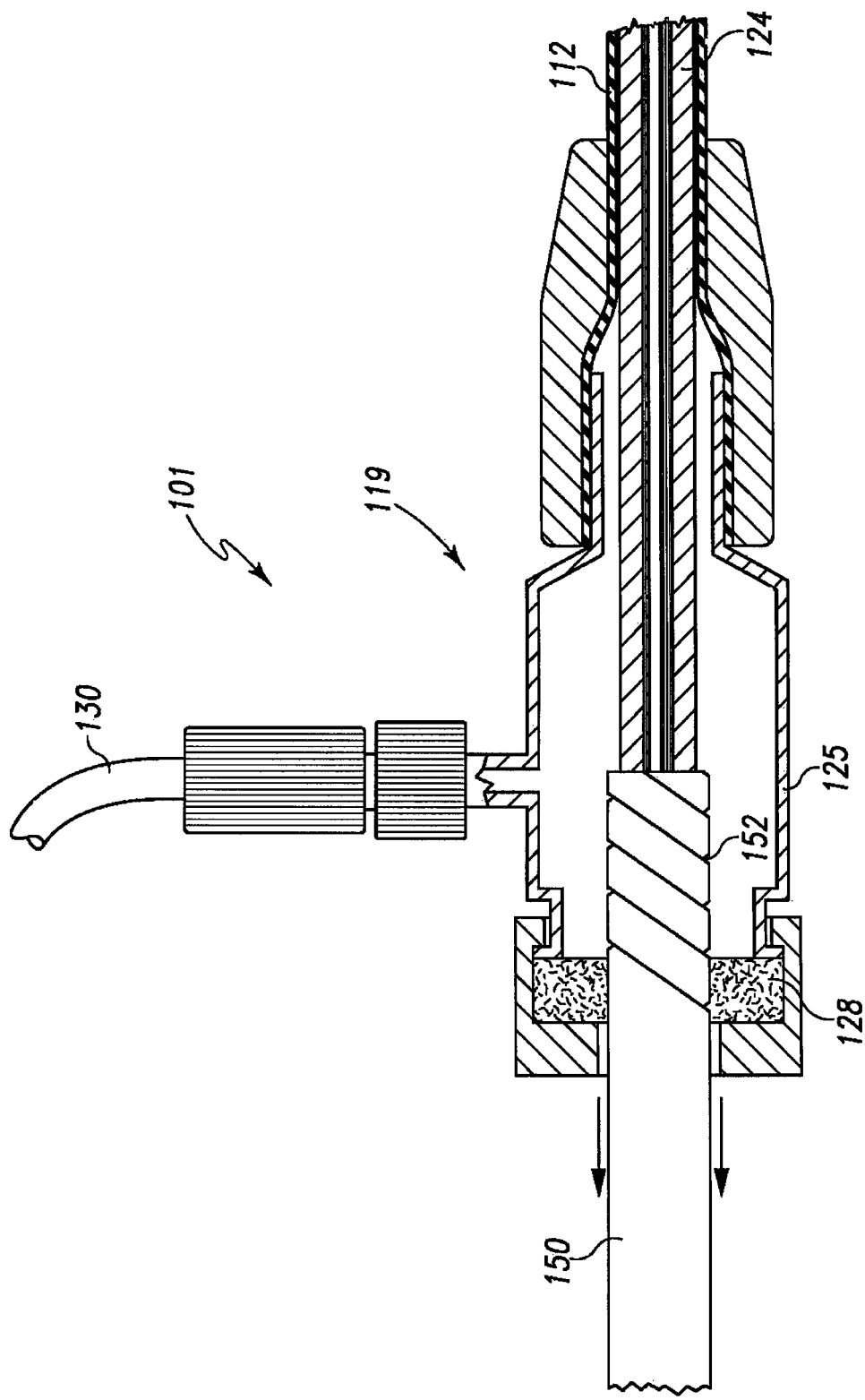

As shown in FIGS. 7 and 8, the sleeve 150 may be provided with one or more grooves 152, or the like, formed on an outside surface of the sleeve 150. The grooves 152 allow the sheath to receive and retain a lubricant. When the sleeve 150 is removed from the housing 125, the valve 128 traverses the sleeve surface and the grooves 152. Lubricant that is present in the grooves 152 traverses, or passes under, the valve 128 and lubricates the valve surface. The grooves 152 may be disposed circumferentially and/or longitudinally along the sleeve 150. For example, in FIG. 7 the sleeve 150 includes a plurality of annular grooves 152 and in FIG. 8 the sleeve 150 includes one or more helical grooves 152. In other examples, a sleeve 150 may be provided and include grooves, such as the grooves 162,166, illustrated in FIG. 9. As used herein, the term "groove" refers to a channel, depression, cut, score, notch, line, perforation, aperture, or the like, and includes both recessed structures as well as projected structures. The term "groove" may also refer to a series of channels, depressions, cuts, scores, notches, lines, perforations, apertures, or the like. A groove may be provided by any mechanical, thermal, or chemical means known in the art, such as cutting by knife or carbide tip, by sanding, by chemical etching, by laser scoring, or by molding.

Figure 9:
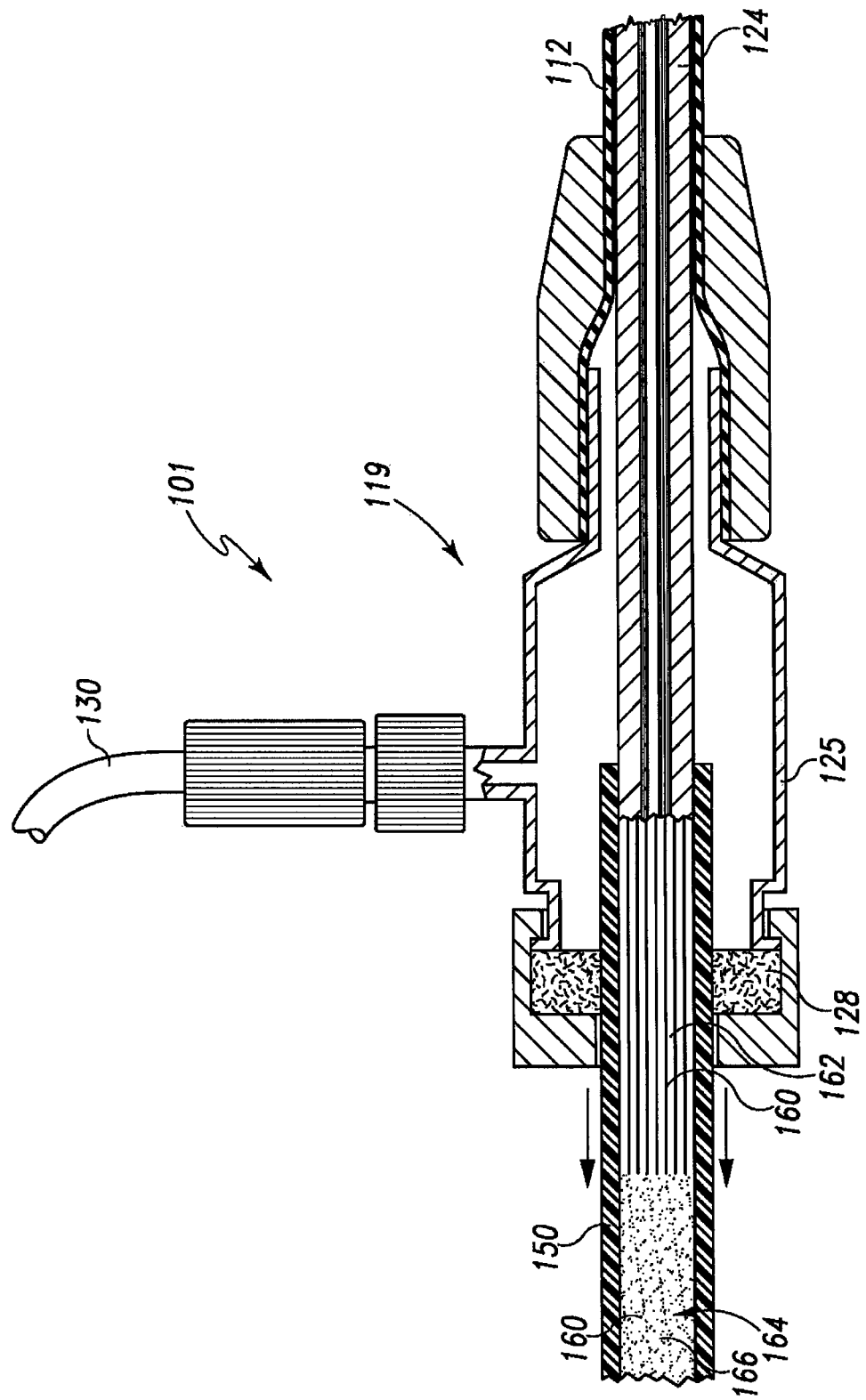

As shown in FIG. 9, the dilator 124 may additionally, or alternatively, include one or more grooves 160 formed on an outside surface of the dilator. The grooves 160 may be disposed circumferentially and/or longitudinally along the dilator 124. For example, in FIG. 9, the dilator 124 has a plurality of substantially longitudinal grooves 162 and a roughened region 164 that includes a plurality of short grooves 166 that provide a roughened or textured surface. The grooves 162, 166 may be provided, for example, to increase the surface area of the dilator 124 and to improve wetting and retention of lubricants.

In some examples, the sleeve 150 and/or the dilator 124 may comprise a lubricant coating. The lubricant may be a liquid lubricant or a solid lubricant and may be applied to a surface by any suitable process, such as dipping or spraying. After the lubricant is applied, it can be cured to form a coating. In one example, a 1% aqueous hyaluronic acid solution may be applied to a surface and cured by drying the solution to remove some or substantially all of the water. In another example, photo polyvinylpyrrolidone may be applied to the dilator and cured by exposing the surface to an ultraviolet light source.

Example 1

The inventors tested delivery and deployment devices comprising valve lubrication mechanisms, as described above. In one example, the mechanism 101 included a peel-away sleeve 150 with circumferential grooves 152, as described above. In addition, the dilator 124 included a plurality of longitudinal grooves 162, and a roughened surface 164, similar to the configuration shown in FIG. 9. The inventors applied an aqueous solution of hyaluronic acid to the grooved surface of the dilator 124. The solution was prepared by diluting 1 part granular hyaluronic acid in 400 parts water. After the solution was applied to the dilator 124, water was evaporated to form a coating having a thickness of approximately 0.2 to 0.4 mils (thousandths of an inch). The sleeve 150 was then placed over the hyaluronic acid coating so that the coating was disposed between the dilator and the valve.

Next, a saline solution was introduced into the valve housing 125 via the side tube 130. The sleeve 150 was then removed from the valve housing 125 by sliding the distal end of the sleeve 150 along the dilator 124, past the valve 128. Saline solution that was present in the circumferential grooves 152 was pulled through the valve, thus wetting the valve surface. Saline solution also traveled along the grooves 162 and roughened surface 164 of the dilator 124, thus wetting the lubricant coating. The hydrated coating became slippery and reduced the static friction between the dilator 124 and the valve 128.

Curve C of FIG. 5 depicts the exceptional results of this experiment, where the peak withdrawal force was approximately 5 Newtons and the withdrawal force was generally consistent. This device and method resulted, surprisingly, in a 95% reduction in the peak withdrawal force compared to the experiment described above and depicted in curve A.

Example 2

In another experiment, the inventors studied the effect of the valve lubrication mechanism on the Zenith® delivery and deployment system. The Zenith® systems are available from Cook Incorporated, Bloomington, Ind., USA. The delivery and deployment device used in the study included a hemostatic valve assembly with three silicone valves. The prosthesis was removed from the delivery and deployment device to enable the inventors to measure only the frictional force between the dilator and the silicone valves.

The inventors tested four types of devices: 1) control devices, 2) "water" devices, 3) "PVP" devices, and 4) "HLA" devices. The control devices included a standard delivery and deployment device, without modification. The "water," "PVP," and "HLA" devices were modified by roughening the outer surface of the PEEL-AWAY® sheath and the outer surface of the dilator. The inventors used sandpaper to apply circumferential grooves to a 0.5 inch length portion of the outer surface of the PEEL-AWAY® sheath, and to apply longitudinal grooves to a 2 inch portion of the dilator. The grooved PEEL-AWAY® sheath was cleaned with a cotton-tipped swab wetted with ethyl alcohol and the grooved dilator was cleaned with a cotton-tipped swab wetted with water.

A 1% HLA/water solution was applied to the grooved dilator surface of the "HLA" devices. The HLA was Sigma 53747-10G, available from Sigma-Aldrich®, St. Louis, Mo., USA. The application was dried in air until it was no longer tacky. A PVP polymer solution was applied to the grooved dilator surface of the "PVP" devices. The PVP was 2002-HC, available from Cook, Incorporated, Bloomington, Ind., USA. The application was cured with ultraviolet light until it was no longer tacky.

The dilators were positioned so that the distal edge of the coating was disposed distal of the silicone valves. Likewise, the PEEL-AWAY® sheaths were positioned so that the distal edge of the sheath was disposed distal of the silicone valves.

Tests were performed on delivery and deployment devices with 14 F, 16 F, and 8 F diameter dilators. The delivery and deployment devices were mounted vertically in a test fixture attached to the base of an Instron machine (available from Instron Corporation, Norwood, Mass., USA). The control devices were prepared by removing the PEEL-AWAY® sheaths and then filling the valve housings with water, consistent with the Instructions for Use for the delivery and deployment device. The "water," "PVP," and "HLA" devices were prepared by filling the valve housings before the PEEL-AWAY® sheaths were removed. The sheaths were then removed to lubricate the silicone valves and the dilator. Then, the valve housings were again filled with water.

Figure 10:
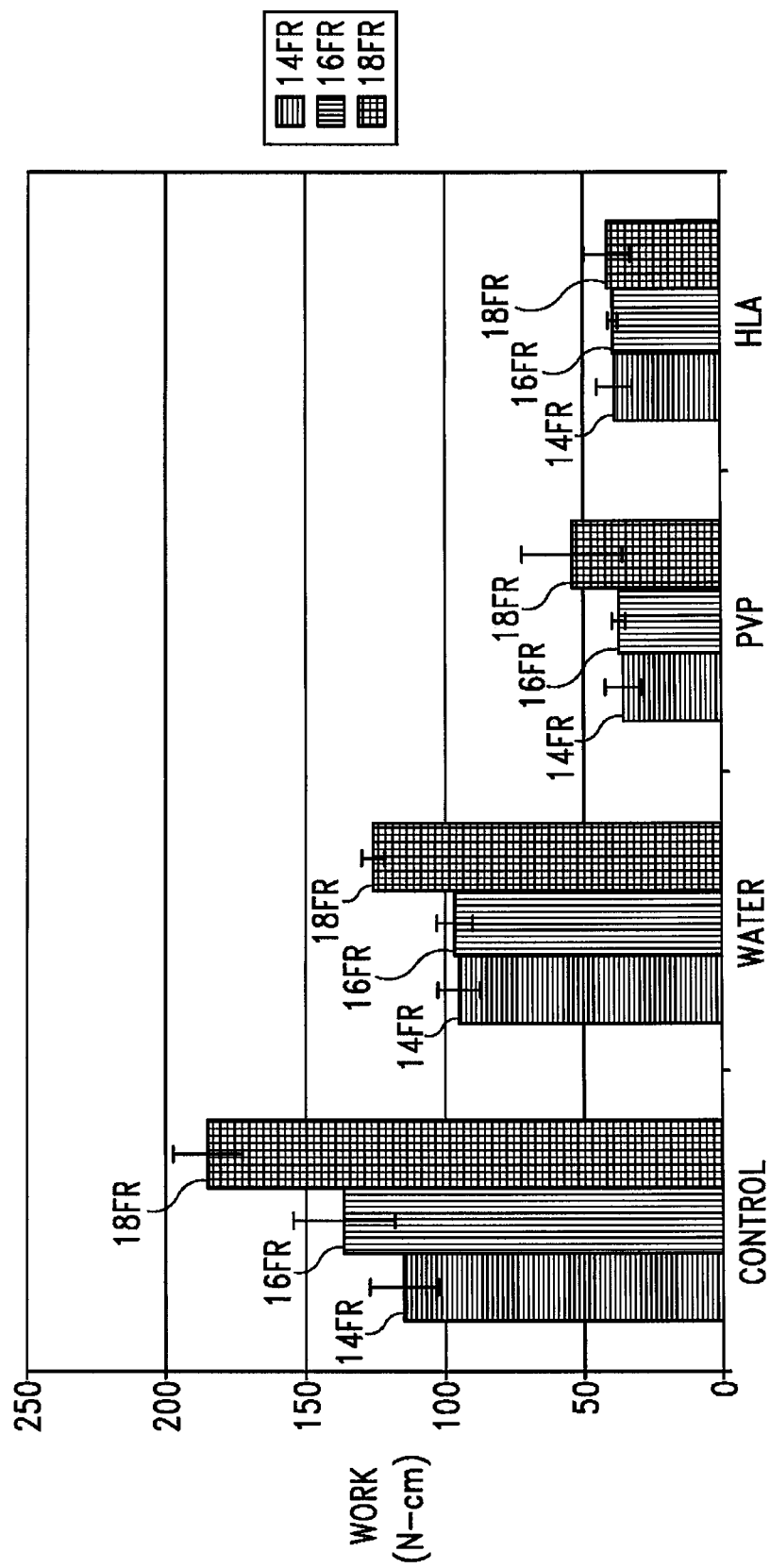
FIG. 10 is a graph depicting the sheath withdrawal energy of various delivery and deployment devices.

The Instron machine and fixture were configured to move the dilator distally through the silicone valves over a distance of approximately 85 mm at a rate of 18 mm per second. The machine measured and recorded the force as a function of displacement. FIG. 10 is a bar chart that depicts the sheath withdrawal energy (N-cm), or the average withdrawal force multiplied by retraction distance. As shown in FIG. 10, the lubrication mechanisms resulted in an overall reduction of the energy required to withdraw the sheath, compared to devices that did not include a lubrication mechanism. The improvements ranged from an approximately 20% reduction in energy for the 14 FR "water" device to an approximately 80% reduction for the 18 FR "HLA" device.

Figure 11:
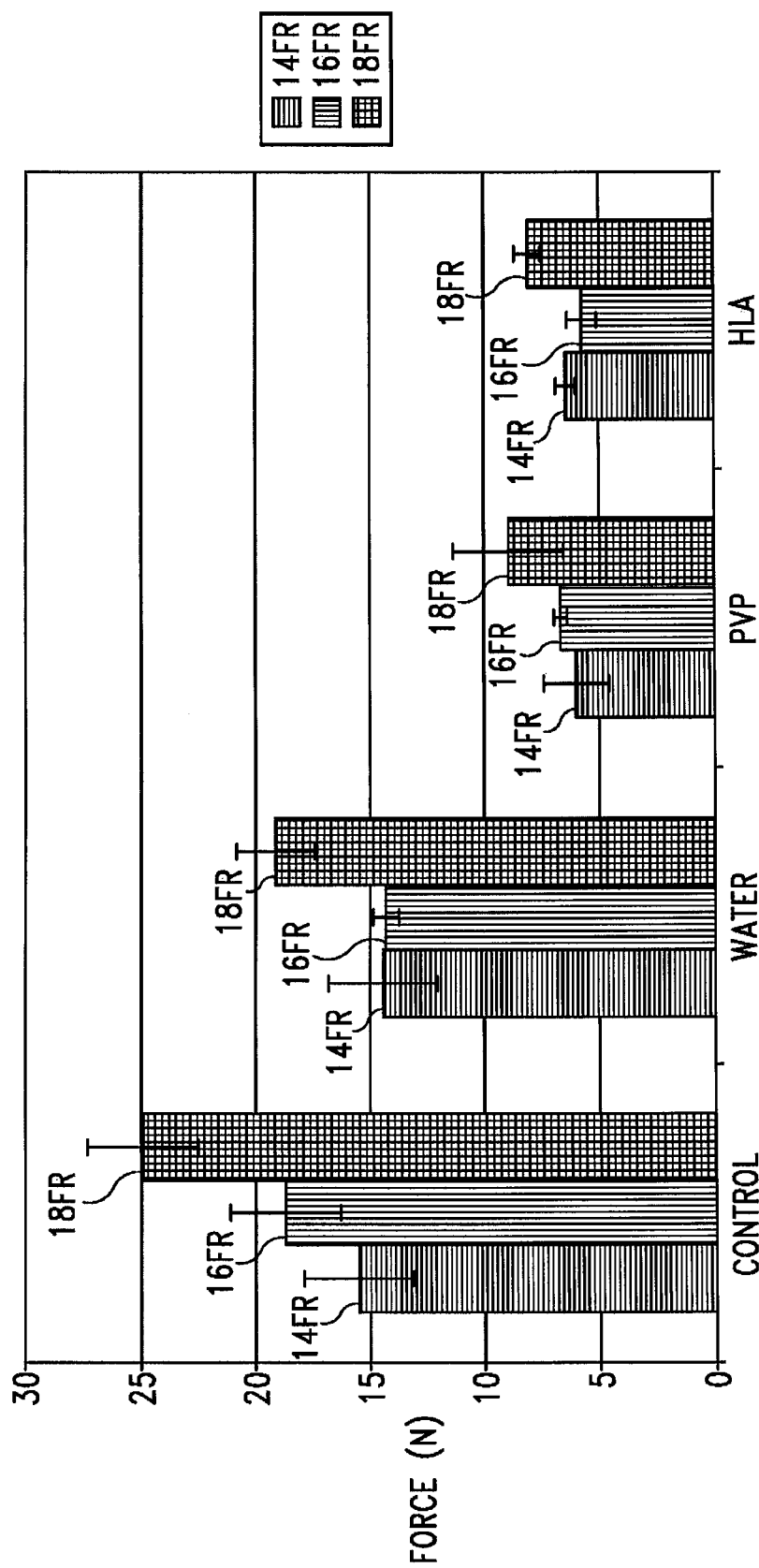
FIG. 11 is a graph depicting the average peak deployment force of various delivery and deployment devices.

FIG. 11 is a bar chart that depicts the average peak deployment force (N) for the various devices. As shown in FIG. 11, the lubrication mechanisms resulted in an overall reduction of the peak force, compared to devices that did not include a lubrication mechanism. The improvements ranged from an approximately 13% reduction for the 14 FR "water" device to an approximately 70% reduction for the 18 FR "HLA" device.

In general, the withdrawal energy and the average peak deployment force increased as the size of the dilator increased. However, for the HLA devices, the results indicate that dilator size was less significant a factor.

Other examples are contemplated and are within the scope of the present invention. For example, as noted above, one of the challenges with using lubricants is that the device may become slippery and difficult to grasp and manipulate. Accordingly, it may be desirable to control the ability of the lubricant to travel along the dilator 124, outside of the housing 125. Therefore, in some examples, the length of the roughened region 164 and the length and extent of the grooves 162, and other aspects of the design may be controlled to limit or prevent lubricant from traveling too far beyond the housing 125. In other examples, the dilator and/or sleeve may be provided without grooves.

Throughout this specification various indications have been given as to preferred and alternative embodiments of the invention. However, it should be understood that the invention is not limited to any one of these. It is therefore intended that the foregoing detailed description be regarded as illustrative rather than limiting, and that it be understood that it is the appended claims, including all equivalents, that are intended to define the spirit and scope of this invention.

What is claimed is:

1. A delivery and deployment device comprising:
   a sheath having a proximal end, a distal end, and a lumen disposed therebetween;
   a dilator having a distal end slidingly disposed within the sheath lumen;
   a valve assembly comprising a valve housing affixed to the sheath and a valve disposed within the housing between the sheath and the dilator; and
   a valve lubrication mechanism disposed between the valve and the dilator and having an inner surface in sliding contact with the outer surface of the dilator and an outer surface in sliding contact with the valve, where the outer surface of the lubrication mechanism comprises one or more grooves for receiving a lubricant.

2. The device of claim 1, where the one or more grooves are annular grooves.

3. The device of claim 1, where the one or more grooves are helical grooves.

4. The device claim 1, further comprising a lubricant.

5. The device of claim 4, where the lubricant is coated on the outer surface of the dilator.

6. The device of claim 4, where the lubricant is water-soluble.

7. The device of claim 4, where the lubricant is selected from the group consisting of hyaluronic acid, polyvinylpyrolidone, and polyacrylamide.

8. A delivery and deployment device comprising:
a sheath having a proximal end, a distal end, and a lumen disposed therebetween;
a dilator having a distal end slidingly disposed within the sheath lumen;
a valve assembly comprising a valve housing affixed to the sheath and a valve disposed within the housing between the sheath and the dilator; and
a valve lubrication mechanism disposed between the valve and the dilator and having an inner surface in sliding contact with the outer surface of the dilator and an outer surface in sliding contact with the valve, where the dilator comprises one or more grooves for receiving a lubricant.

9. The device of claim 8, where the one or more dilator grooves are longitudinal grooves and/or circumferential grooves.

10. The device claim 8, further comprising a lubricant.

11. The device of claim 10, where the lubricant is coated on the outer surface of the dilator.

12. The device of claim 10, where the lubricant is water-soluble.

13. The device of claim 10, where the lubricant is selected from the group consisting of hyaluronic acid, polyvinylpyrolidone, and polyacrylamide.

14. A delivery and deployment device comprising:
a sheath having a proximal end, a distal end, and a lumen disposed therebetween;
a dilator having a distal end slidingly disposed within the sheath lumen;
a valve assembly comprising a valve housing affixed to the sheath and a valve disposed within the housing between the sheath and the dilator; and
a valve lubrication mechanism disposed between the valve and the dilator and having an inner surface in sliding contact with the outer surface of the dilator and an outer surface in sliding contact with the valve, and any two or more of the following:
the outer surface of the lubrication mechanism comprises one or more grooves for receiving a lubricant;
the one or more grooves are annular grooves;
the one or more grooves are helical grooves;
the dilator comprises one or more grooves for receiving a lubricant;
the one or more dilator grooves are longitudinal grooves and/or circumferential grooves;
a lubricant;
a water-soluble lubricant;
a lubricant coated on the outer surface of the dilator; and
a lubricant selected from the group consisting of hyaluronic acid, polyvinylpyrolidone, and polyacrylamide.

15. A delivery and deployment device comprising:
a sheath having a proximal end, a distal end, and a lumen disposed therebetween;
a dilator having a distal end slidingly disposed within the sheath lumen;
a valve assembly comprising a valve housing affixed to the sheath and a valve disposed within the housing between the sheath and the dilator; and
a means for lubricating the contact surface between the valve and the dilator
where the lubricating means comprise a sleeve having an inner surface in sliding contact with the outer surface of the dilator and an outer surface in sliding contact with the valve and where the outer surface of the sleeve comprises one or more grooves for receiving a lubricant.

16. The device of claim 15, further comprising a lubricant coated on the outer surface of the dilator.

17. A method of reducing the sheath withdrawal force of a delivery and deployment device comprising an elongate sheath, a dilator slidingly disposed within a lumen of the sheath, and a valve assembly comprising a valve for forming a hemostatic seal between the sheath and the dilator, the method comprising the steps of:
providing a valve lubrication mechanism; and
sliding the valve lubrication mechanism between the dilator and the valve to lubricate the contact surface between the dilator and the valve,
wherein the outer surface of the lubrication mechanism comprises one or more grooves for receiving a lubricant or wherein the dilator comprises one or more grooves for receiving a lubricant.

18. The method of claim 17, further comprising the step of applying a lubricant to the valve lubrication mechanism.

19. The method of claim 17, further comprising the step of applying a lubricant to the dilator.

20. The method of claim 19, further comprising the step of evaporating a solvent from the lubricant to form a coating.

21. The method of claim 20, further comprising the step of re-solubilizing the coating.

22. The method of claim 17, further comprising any two or more of the following steps:
applying a lubricant to the valve lubrication mechanism;
applying a lubricant to the dilator;
evaporating a solvent from the lubricant to form a coating; and
re-solubilizing the coating.

* * * * *